(12) United States Patent
Pickenhagen et al.

(10) Patent No.: US 7,176,176 B2
(45) Date of Patent: *Feb. 13, 2007

(54) 2-METHYL-4-PHENYL-1,3-DIOXOLANE

(75) Inventors: Wilhelm Pickenhagen, Höxter (DE);
Dietmar Schatkowski, Stadtoldendorf (DE)

(73) Assignee: Symrise GmbH & Co. KG, Holzminden (DE)

( * ) Notice: Subject to any disclaimer, the term of this patent is extended or adjusted under 35 U.S.C. 154(b) by 358 days.

This patent is subject to a terminal disclaimer.

(21) Appl. No.: 10/402,754

(22) Filed: Mar. 28, 2003

(65) Prior Publication Data

US 2003/0215478 A1 Nov. 20, 2003

Related U.S. Application Data

(63) Continuation of application No. 09/738,338, filed on Dec. 15, 2000.

(30) Foreign Application Priority Data

Dec. 17, 1999 (DE) ................................. 199 61 431

(51) Int. Cl.
*A61K 8/00* (2006.01)
*A23L 2/56* (2006.01)
(52) U.S. Cl. ........................ 512/12; 426/536; 426/534; 512/8
(58) Field of Classification Search ................. 514/463; 549/430
See application file for complete search history.

(56) References Cited

FOREIGN PATENT DOCUMENTS

DE 109176 2/1990

OTHER PUBLICATIONS

Zhu et al. "Organometallic Catalysis: Formation of 1,3-Dioxolanes and Their Analogs Catalyzed by Methylrhenium Trioxide (MTO)" 1997, Organometallics, 16, 3658-63.*
M. Hojo, H. Aihara, Y. Suginohara, K. Sakata, Sh. Nakamura, Ch. Murakami and A. Hosomi: A new and mild system for the generation of nonstabilized carbonyl yields: Synthetically practical use in reactions with electron-deficient dipolarophiles. J. Org. Chem. 1997, 8610-8611.
K. Kulka, J. W. Dittick: Acetals and ketals of 1-phenyl-1,2-ethanediol. Int. Congr. Essent. Oils, 6th 1974, 72, 11 pp.

* cited by examiner

*Primary Examiner*—Sreeni Padmanabhan
*Assistant Examiner*—Gina C Yu
(74) *Attorney, Agent, or Firm*—Akerman Senterfitt; Stephan A. Pendore

(57) ABSTRACT

The sensory properties of the diastereomeric enantiomer pairs and of the pure enantiomers of the compound 2-methyl-4-phenyl-1,3-dioxolane are described. The cis compounds (2R,4S)-2-methyl-4-phenyl-1,3-dioxolane and (2S,4R)-2-methyl-4-phenyl-1,3-dioxolane are the most sensorially valuable. These enantiomers and mixtures thereof are particularly suitable for use as a sensorially active substance, for example as a fragrance.

1 Claim, 3 Drawing Sheets

2-METHYL-4-PHENYL-1,3-DIOXOLANE

REFERENCE TO RELATED APPLICATIONS

This application is a continuation of application Ser. No. 09/738,338 filed Dec. 15, 2000.

BACKGROUND OF THE INVENTION

1. Field of the Invention

The present invention relates to the compound 2-methyl-4-phenyl-1,3-dioxolane, and to certain diastereomeric enantiomer pairs and to enantiomers of this compound.

2. Description of the Related Art

2-Methyl-4-phenyl-1,3-dioxolane is known. As early as 1900, the German Patent Specification 109176 (Albert Verley) was published, in which the synthesis of 2-methyl-4-phenyl-1,3-dioxolane in strongly protic media, but not the isomer distribution of the resulting mixture, is described; the odor of 2-methyl-4-phenyl-1,3-dioxolane, which is not defined in more detail with regard to its composition, is referred to as a jasmine odor in DE 109176.

In 1975, K. Kulka and J. W. Dittrick reported extensively on the sensory properties of a large number of synthesized acetals [K. Kulka, J. W. Dittrick, Cosmetics & Perfumery, Vol. 90, 90–95, (1975)]. However, the sensory evaluation of the synthesized acetals was again only undertaken by reference to the diastereomer mixtures. Isolation of the epimers or enantiomers from the mixtures or the synthesis thereof was not carried out, nor were the epimers or enantiomers sensorially evaluated.

Despite being known for a long time, 2-methyl-4-phenyl-1,3-dioxolane (as diastereomer mixture as described in DE 109176) is currently not a fragrance which is available commercially. This is due in particular to the presence of undesired chocolate notes which do not harmonize with the basic jasmine odor and lead to an unclean sensory overall character.

SUMMARY OF THE INVENTION

The object of the present invention was therefore to provide a sensorially active substance (fragrance and/or flavor) which has a powerful floral and/or jasmine odor, but, compared with the odor of 2-methyl-4-phenyl-1,3-dioxolane (as described in DE 109176 or by Kulka and Dittrick in Cosmetics & Perfumery), has only attenuated chocolate notes, or none at all.

This object is achieved by providing the enantiomers (2R,4S)-2-methyl-4-phenyl-1,3-dioxolane and (2S,4R)-2-methyl-4-phenyl-1,3-dioxolane, which have hitherto neither been isolated nor investigated with regard to their sensory properties. Both compounds have strong sensory activity and, surprisingly, an odor which does not include an undesired chocolate note. The enantiomers according to the invention can therefore be advantageously used in perfume compositions of any odor type both as one of the main components and also in the trace range. Use in flavor compositions is likewise possible.

The invention is based on the surprising finding that diastereomer mixtures of 2-methyl-4-phenyl-1,3-dioxolane have very characteristic odiferous properties depending on the choice of reaction conditions, and differ significantly from one another.

In particular, it has been found that diastereomer mixtures of 2-methyl-4-phenyl-1,3-dioxolane (cf. the general formula (4) in FIG. 1) which have a comparatively high proportion of cis isomers (cf. formula (4a) in FIG. 1) are sensorially more valuable than diastereomer mixtures which have a particularly high proportion of trans isomers (cf. formula (4b) in FIG. 1).

DETAILED DESCRIPTION OF THE INVENTION

Preferred sensorially active substances (preferred fragrances or flavors) are mixtures which comprise one part by weight of cis enantiomers (4a), i.e. (2R,4S)-2-methyl-4-phenyl-1,3-dioxolane and/or (2S,4R)-2-methyl-4-phenyl-1,3-dioxolane and less than two, preferably less than one, parts by weight of trans enantiomers (4b), i.e. (2R,4R)-2-methyl-4-phenyl-1,3-dioxolane and/or (2S,4S)-2-methyl-4-phenyl-1,3-dioxolane. The weight ratio of cis enantiomers (4a) to trans enantiomers (4b) should therefore be at least greater than 1:2, but preferably even greater than 1:1.

The preferred mixture of the cis isomers (4a) has a strong, animal, narcotically-green odor reminiscent of hyacinths. The after-odor here has clearly woody, ozone-like odor properties.

By contrast, the less preferred mixture of the trans isomers (4b) has weak, slightly animal odor effects with clearly defined odor impressions, clearly reminiscent of chocolate.

Figure 2:
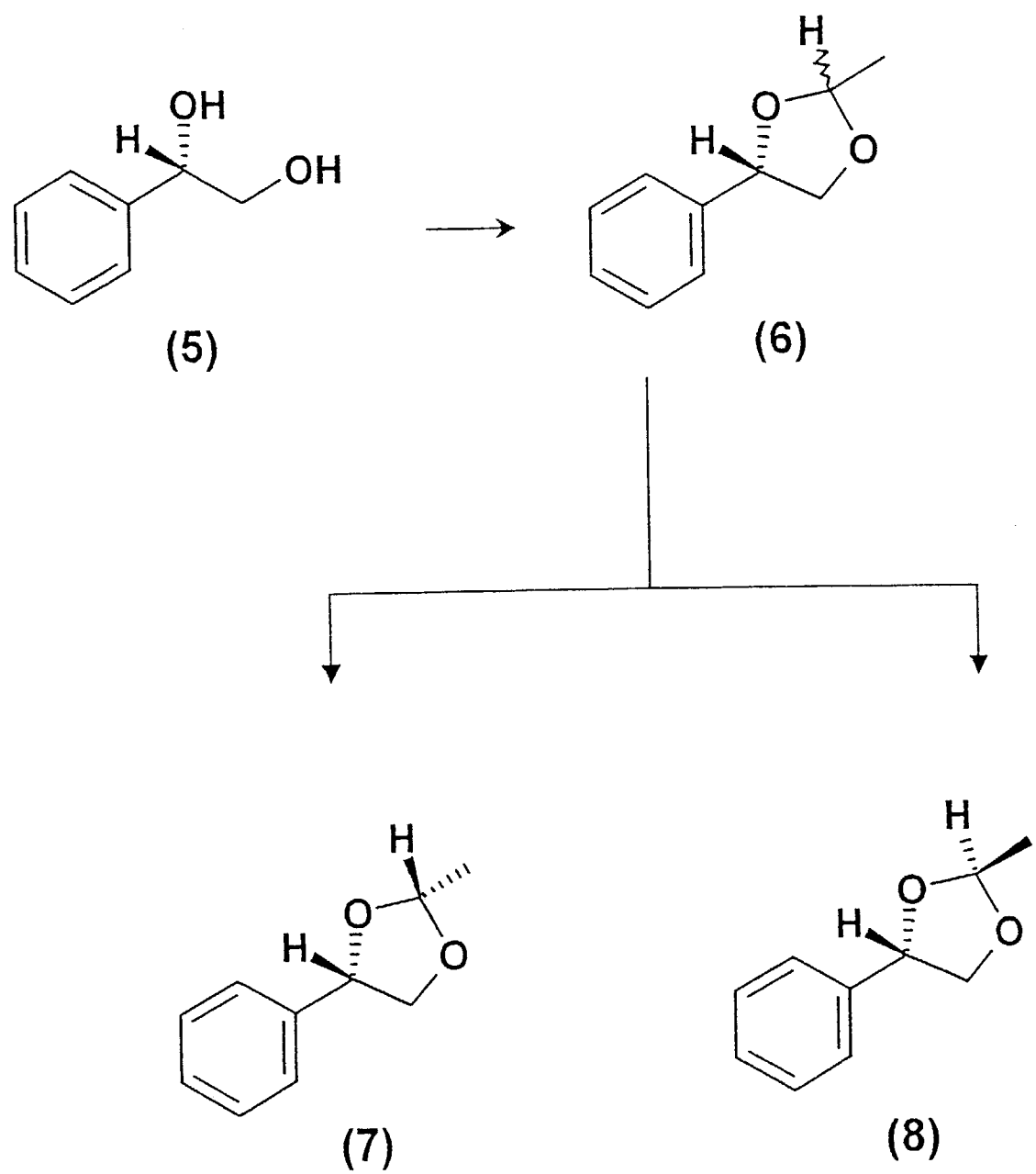
FIGS. 2 and 3 illustrates the process by which enantiomerically pure diols 5 (FIG. 2) and 9 (FIG. 3) are converted to epimeric acetals 7, 8, 11 and 12, respectively.
Figure 3:
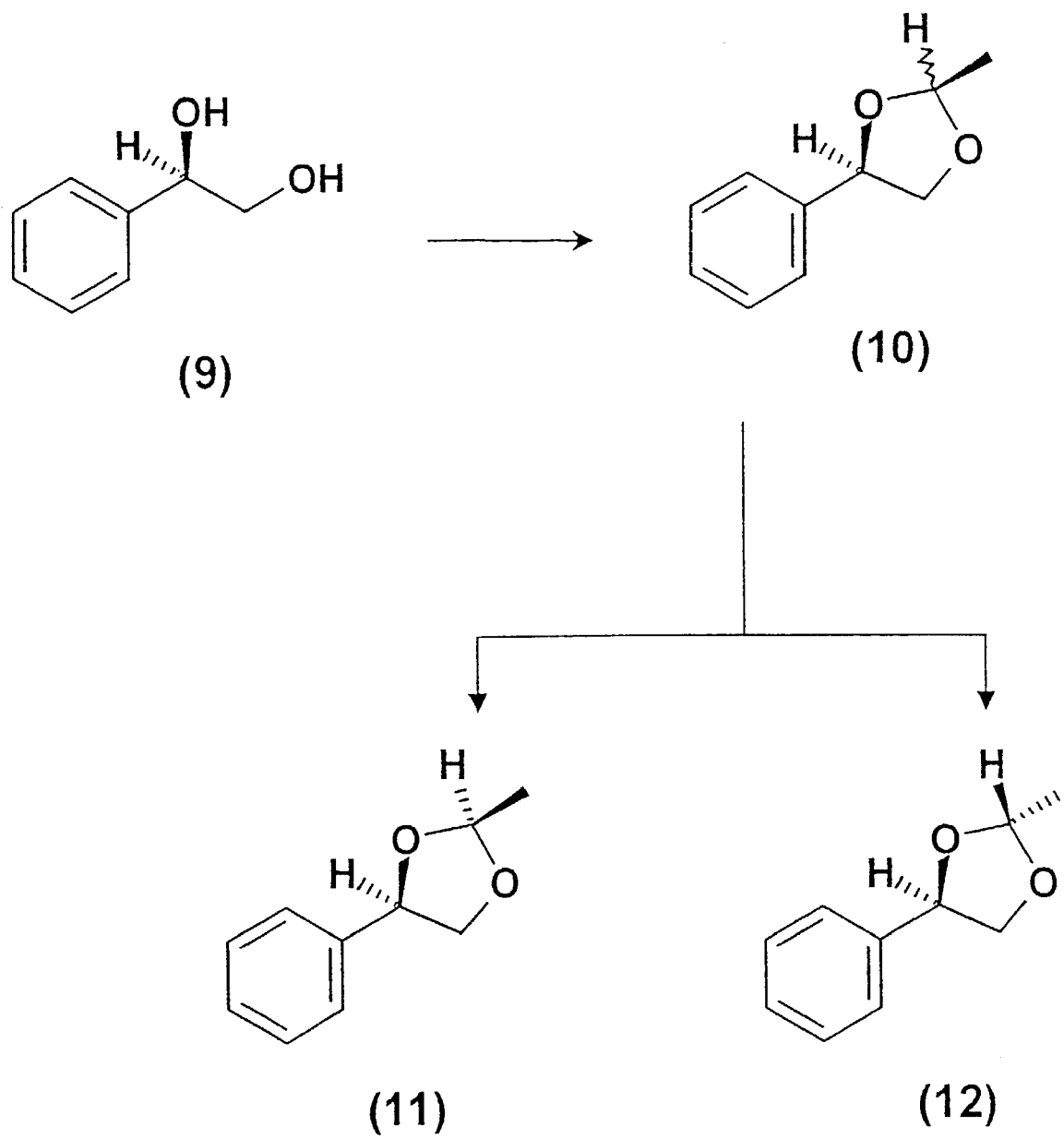

It is likewise possible to clearly differentiate between the sensory properties of the pure enantiomers accessible from the epimer series (2R,4S)-2-methyl-4-phenyl-1,3-dioxolane (cis; cf. formula (7) in FIG. 2), (2S,4R)-2-methyl-4-phenyl-1,3-dioxolane (cis; cf. formula (11) in FIG. 3) or (2R,4R)-2-methyl-4-phenyl-1,3-dioxolane (trans; cf. formula (8) in FIG. 2), (2S,4S)-2-methyl-4-phenyl-1,3-dioxolane (trans; cf. formula (12) in FIG. 3).

Thus, the acetal 7 (cf. FIG. 2) accessible from S(+)-1-phenyl-1,2-ethanediol according to FIG. 2 and Examples 3 or 5 below and having a strong, clear, indole-like note, which has distinct aspects of rose and jasmine, has been assessed as the isomer with the best smell and, on the basis of the odor threshold, as the strongest isomer. For the odor evaluation of the individual enantiomers, cf. Examples 13 and 14 below.

To prepare 2-methyl-4-phenyl-1,3-dioxolane of the general formula (4) (FIG. 1), styrene (1) was converted in the usual manner into styrene oxide (2), and the latter was converted into 1-phenyl-1,2-ethanediol (3) in a likewise known manner. The latter could then be converted into a mixture (4) of the diastereomeric acetals (+/−) 4a/ (+/−) 4b (FIG. 1) in a known manner.

Starting from the commercially available enantiomerically pure diols 5 (FIG. 2) and 9 (FIG. 3), the epimeric acetals 7, 8 and 11, 12 respectively were obtainable.

The isomer composition of the synthesized acetals (+/−) 4a, (+/−) 4b; 7, 8; 11, 12 is subject, as a comparison of Examples 2, 9, 10, 11 and 12 below, in particular, shows, to a strong temperature effect. Low temperatures favor the formation of the sensorially more valuable cis compounds ((+/−) 4a, 7, 11), while high temperatures favor that of the sensorially undesired trans compounds (+/−) 4b, 8, 12. Thus, at −70° C., a diastereomer mixture with a weight ratio of 90:10 ((+/−) 4a: (+/−) 4b (Example 12)) was obtained, while in boiling xylem (160° C.),only a diastereomer mixture with a weight ratio of 38:62 ((+/−) 4a: (+/−) 4b (Example 10)) was obtained. Starting from the enantiomerically pure diols, corresponding isomer mixtures (7:8; 11:12) were found. Here, the isomer ratios are constantly fluctuating depending on the temperature.

The acetal-formation reactions were carried out in the presence of protic acids, such as e.g. HCl, $H_2SO_4$ or para-toluenesulfonic acid, and in customary solvents, such as e.g. hexane, toluene, diethyl ether or methanol.

From the racemic or epimerically pure diastereomer mixtures, the four individual enantiomers were isolated in pure form by chromatographic or distillative methods. From the pure enantiomers it is possible to prepare mixtures with any mixing ratios. Because of the results found, mixtures with a high proportion of the cis compounds (+/−) 4a, 7, 11 are preferred (particularly for the preparation of fragrance compositions).

It remains to be mentioned that, for the preparation of the sensorially valuable compounds or compound mixtures, (2R,4S)-2-methyl-4-phenyl-1,3-dioxolane (7) and/or (2S,4R)-2-methyl-4-phenyl-1,3-dioxolane (11) also the respective epimers with identical C4 configuration (2S,4S)-2-methyl-4-phenyl-1,3-dioxolane (8) and/or (2R,4R)-2-methyl-4-phenyl-1,3-dioxolane (12), dissolved in a solvent, can be brought to a temperature of 20° C. or less, preferably 0° C. or less, and then maintained at this temperature until the desired or maximum amount of the target product has formed.

The examples below serve to illustrate the invention:

EXAMPLE 1

Figure 1:
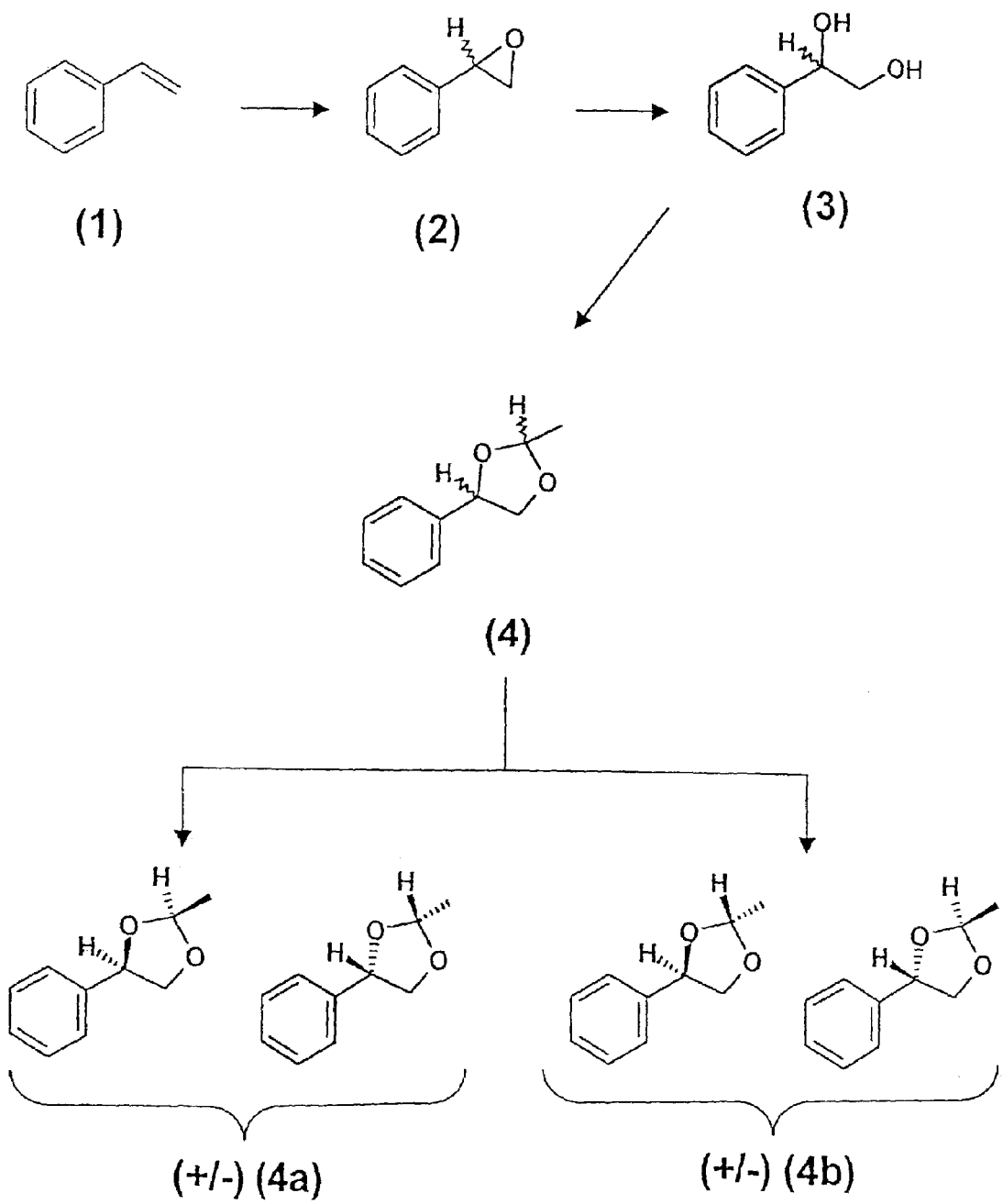
FIG. 1 shows diasteriomer mixtures, cis isomers and trans isomers.

Preparation of (±)-1-phenyl-1,2-ethanediol (3)—FIG. 1

A 2 l stirrer fitted with reflux condenser, thermometer and dropping funnel was charged with 600 g of 0.1% strength $H_2SO_4$ and 2 g of tetrabutylammonium hydrogensulfate, and then, at 20° C. to 25° C., 200 g (1.67 mol) of styrene oxide (2) were added over the course of 1 h. When the dropwise addition was complete, the mixture was then stirred for 2 h and then worked up. 200 ml of diethyl ether were added to the reaction mixture, and the organic phase was washed until neutral with sodium carbonate solution and water, and dried over $Na_2SO_4$, and the solvent was distilled off under reduced pressure, leaving 223 g of crude product (91% pure according to GC).

Gas chromatogram (Shimadzu GC14A DB1, 30 N, 30 m, 100–240° C., 10° C.×min$^{-1}$)

The crude product was solid (m.p.: 65–67°).

EXAMPLE 2

Preparation of (±)-2-methyl-4-phenyl-1,3-dioxolane (4) (reaction temperature: 5° C. to 20° C.)—FIG. 1

A 1 l stirrer fitted with reflux condenser, thermometer and dropping funnel was charged with 223 g (1.47 mol) of (±)-1-phenyl-1,2-ethanediol (3) (91% pure according to GC) from Example 1, 100 ml of diethyl ether and 2 g of para-toluenesulfonic acid and cooled to 5–10° C., and, at this temperature, 80.8 g (1.83 mol) of acetaldehyde were added over the course of 30 min. When the dropwise addition was complete, the mixture was then stirred firstly for 4 h at 5–10° C. and for a further 2 h at a maximum of 20° C. After this time, water was added, the organic phase was separated off, the aqueous phase was extracted with 1×100 ml of ether, and the combined organic phases were washed until neutral with sodium carbonate solution and water. Drying over $Na_2SO_4$ was then carried out, and the solvent was distilled off under reduced pressure.

This gave 238 g of crude product (84.3% pure according to GC).

Gas chromatogram (HP 5970B, DBWAX 60 N, 60 m, 60–240° C., 4° C./min)

The mixture consisted of 2 diastereomeric enantiomer pairs.

(+/−) 4a $R_t$=28.81 min=54.6%
(+/−) 4b $R_t$=29.24 min=29.7%
(+/−) 4a:(+/−) 4b ratio 65:35.

The formation of the (sensorially valuable) cis compound (4a) was therefore preferred over the formation of the (sensorially undesired) trans compound (4b).

Distillation of 100 g of crude product over a 40 cm metal packed column gave 78 g of (4) (98' pure according to GC), b.p.$_{.3\ mm}$=90–92° C.

(+/−) 4a $R_t$=28.8 min=65.7%
(+/−) 4b $R_t$=29.24 min=32.3%

Distillation of 100 g of crude product over a Fischer Spaltrohr column produced 28.4 g (93% pure according to GC) of (+/−) 4a and 18.4 g (89.4% pure according to GC) of (+/−) 4b.

GC/MS: HP 5970, B, DBWAX 60 N, 60 m, 60–240° C., 4° C./min (+/−) 4a $R_t$=28.85 min, b.p.$_{.4\ mbar}$=89–90° C.

MS: m/z (%)=164 (14, M+), 134 (45), 121 (25), 120 (80), 119 (27), 104 (49), 103 (32), 91 (47), 58 (100), 43 (47)

$^{13}$C-NMR (CDCl$_3$), Varian VXR-300: δ [ppm]: 19.86 ($\underline{C}H_3$), 71.93 ($\underline{C}H_2$), 78.26, 102.28, ($\underline{C}H$), 126.19, 127.91, 128.4 ($\underline{C}H$-aromatic).

(+/−) 4b $R_t$=29.2 min, b.p.$_{.4\ mbar}$=91–92° C.

MS: m/z (5)=164 (15, M+), 134 (38), 121 (33), 120 (70), 104 (52), 103 (41), 91 (46), 77 (24), 58 (100), 43 (46).

$^{13}$C-NMR (CDCl$_3$), Varian VXR-300: δ [ppm]: 20.35 ($\underline{C}H_3$), 72.72 ($\underline{C}H_2$) 77.37, 10256 ($\underline{C}H$), 125.81, 127.76, 128.48, 128.51 ($\underline{C}H$, aromatic).

EXAMPLE 3

Preparation of an Epimer Mixture of (2R,4S)-2-methyl-4-phenyl-1,3-dioxolane (7) and (2S,4S)-2-methyl-4-phenyl-1,3-dioxolane (8)—FIG. 2

A 100 ml stirrer fitted with reflux condenser, thermometer and dropping funnel was charged with 2 g (14.47 mmol) of S(+)-1-phenyl-1,2-ethanediol (Fluka [α D/20°+39±1°]), 10 ml of diethyl ether and 20 mg of para-toluenesulfonic acid and cooled to 5–10° C., and, at this temperature, 0.96 g (21.7 mmol) of acetaldehyde were added dropwise over a period of 15 min. After the mixture had then been stirred for 2 h at this temperature, 5 ml of sodium chloride solution were added and the mixture was worked up. The reaction mixture was extracted with 2×10 ml of ether, the combined organic phases were washed until neutral with sodium carbonate solution and water and dried over $Na_2SO_4$, and the solvent was distilled off under reduced pressure, giving 2.12 g of crude product (96% pure according to GC).

GC: conditions see Example 2

7 $R_t$=28.86 min=67.2%

8 $R_t$=29.24 min=28.8%

7:8 ratio=70:30

EXAMPLE 4

Preparation of an Epimer Mixture of (2S,4R)-2-methyl-4-phenyl-1,3-dioxolane (11) and (2R,4R)-2-methyl-4-phenyl-1,3-dioxolane (12)—FIG. 3

A 100 ml stirrer fitted with reflux condenser, thermometer and dropping funnel was charged with 2 g (14.47 mmol) of R(−)-1-phenyl-1,2-ethanediol (Fluka), [α D/20°−39±1°]), 10 ml of diethyl ether, 20 mg of para-toluenesulfonic acid and cooled to 5–10° C., and, at this temperature, 0.96 g (21.7 mmol) of acetaldehyde were added over the course of 15 min. The mixture was then stirred for 2 h at this temperature, and 5 ml of sodium chloride solution were added, and the mixture was worked up. The reaction mixture was extracted with 2×10 ml of ether, the combined organic phases were washed until neutral with sodium carbonate solution and water and dried over $Na_2SO_{41}$ and the solvent was distilled off under reduced pressure, leaving 2.09 g of crude product (93.8% pure according to GC).

GC: conditions see Example 2

11 $R_t$=28.82 min=66.1%

12 $R_t$=29.23 min=27.7%

11:12 ratio=70:30

EXAMPLE 5

Alternative Preparation of an Epimer Mixture of (2R,4S)-2-methyl-4-phenyl-1,3-dioxolane (7) and (2S,4S)-2-methyl-4-phenyl-1,3-dioxolane (8)—FIG. 2

2 g (14.47 mmol) of S(+)-1-phenyl-1,2-ethanediol (Fluka [α D/20°+39±1°]), 20 ml of toluene, 20 mg of para-toluenesulfonic acid and 0.76 g (5.8 mmol) of paraldehyde were stirred over a period of 3 h under reflux (110° C.) in a 100 ml stirrer fitted with water separator, reflux condenser and thermometer. After this time, the mixture was cooled to 20° C. and washed until neutral with sodium carbonate solution and water. The solvent was distilled off under reduced pressure, leaving 2.03 g of crude product (91.8% pure according to GC).

GC: conditions see Example 2

7 $R_t$=28.81 min=45.9%

8 $R_t$=29.21 min=45.9%

7:8 ratio=50:50

EXAMPLE 6

Alternative Preparation of an Epimer Mixture of (2S,4R)-2-methyl-methyl-4-phenyl-1,3-dioxolane (11) and (2R,4R)-2-methyl-4-phenyl-1,3-dioxolane (12)—FIG. 3

2 g (14.47 mmol) of R(−)-1-phenyl-1,2-ethanediol (Fluka [α D/20°−39±1°]), 20 ml of toluene, 20 mg of para-toluenesulfonic acid and 0.76 g (5.8 mmol) of paraldehyde were stirred over a period of 3 h under reflux (110° C.) in a 100 ml stirrer fitted with water separator, reflux condenser and thermometer. After this time, the mixture was cooled to 20° C. and washed until neutral with sodium carbonate solution and water, and the solvent was distilled off under reduced pressure, leaving 2.09 g of crude product (92.6% pure according to GC).

GC: conditions see Example 2

11 $R_t$=28.83 min=46.2%

12 $R_t$=29.24 min=46.4%

11:12 ratio=50:50

EXAMPLE 7

Isolation and Analysis of the Epimers from Example 5—FIG. 2

2.03 g of crude acetal mixture (epimer mixture) from Example 5 (purity according to GC 7: 45.9%; 8: 45.9%) were purified by duplicate flash chromatography.

Chromatography Conditions:

150 g of silica gel 60, particle size 0.04–0.063 mm (Merck, art. no. 9385), mobile phase benzene/ethyl acetate 95:5, initial weight: 2.03 g, yield: 208 mg $R_t$=28.8 min (7)=90% pure according to GC, 156 mg $R_t$=29.21 min (8)=91% pure according to GC GC/MS: HP 5970, B, DBWAX 60 N, 60 m, 60–240° C., 4° C./min, 7 $R_t$=28.4 min. MS: m/z (%)=164 (15, M+), 134 (41), 121 (36), 120 (76), 119 (26), 104 (57), 103 (44), 91 (49), 77 (25), 58 (100), 43 (46), $^{13}$C-NMR (CDCl$_3$), Varian VXR-300: δ [ppm]: 19–83 (CH$_3$), 71.98 (CH$_2$) 78.37, 102.38 (CH), 126.28, 127.86, 128.48 (CH-aromatic). 8 $R_t$=29.1 min MS: m/z (%)=164 (12, M+), 134 (44), 121 (25), 120 (73), 119 (27), 104 (49), 103 (33), 91 (47), 90 (29), 58 (100), 43 (45). $^{13}$C-NMR (CDCl$_3$), Varian VXR-300: δ [ppm]: 20.35 (CH$_3$), 72.77 (CH$_2$) 77.47, 102.64 (CH), 125.85, 127.89, 128.51, 128.57 (CH-aromatic).

EXAMPLE 8

Isolation and Analysis of the Epimers from Example 6—FIG. 3

1 g of crude acetal mixture (epimer mixture) from Example 6 was purified by triplicate flash chromatography.

Chromatography Conditions:

150 g of silica gel 60, particle size 0.04–0.063 mm (Merck, Art. No. 9385). Mobile phase benzine/ethyl acetate (98:2), initial weight 1 g; yield 78 mg of 11. 11 $R_t$=28.4 min MS: m/z (%)=164 (11, M+), 134 (46), 121 (26), 120 (77), 119 (28), 104 (50), 103 (32), 91 (48), 90 (31), 58 (100), 43 (46). $^{13}$C-NMR (CDCl$_3$), Varian VXR-300: δ [ppm]: 19.86 (CH$_3$), 71.98 (CH$_2$), 78.34, 102.36 (CH), 126.23, 127.99, 128.48 (CH-aromatic).

Yield: 65 mg of 12

12 $R_t$=29.0 min

MS: m/z (5)=164 (12, M+), 134 (41), 121 (35), 120 (73), 119 (24), 104 (54), 103 (42), 91 (46), 77 (24); 58 (100), 43 (44).

$^{13}$C-NMR (CDCl$_3$), Varian VXR-300: δ [ppm]: 20.34 (CH$_3$), 72.78 (CH$_2$) 77.49, 102.66 (CH), 125.87, 127.92, 128.53, 128.56 (CH-aromatic).

EXAMPLE 9

Alternative Preparation of (±)-2-methyl-4-phenyl-1,3-dioxolane (4) (reaction temperature: 110° C.)—FIG. 1

100 g (0.63 mol) of (±)-1-phenyl-1,2-ethanediol (3) (87% pure according to GC) according to Example 1, 200 ml of toluene, 32 g (0.24 mol) of paraldehyde and 1 g of para-toluenesulfonic acid were charged to a 1 l stirrer, heated to boiling (110° C.) and stirred under reflux for a period of 4 h. A total of 10 ml of water were eliminated. After this time, the mixture was cooled to 20° C. and washed until neutral with sodium carbonate solution and water, and the solvent was distilled off under reduced pressure, leaving 103 g of crude product (85.3% pure according to GC). GC conditions see Example 2.

(+/−) 4a $R_t$=28.8 min=43.5%

(+/−) 4b $R_t$=29.2 min=41.8%

(+/−) 4a (+/−) 4b ratio=51:49.

Virtually identical amounts of the (sensorially valuable) cis compound and of the (sensorially undesired) trans compound were thus produced.

EXAMPLE 10

Alternative Preparation of (±)-2-methyl-4-phenyl-1,3-dioxolane (4) (reaction temperature: 160° C.)—FIG. 1

69 g (0.45 mol) of (±)-1-phenyl-1,2-ethanediol (3) (90% pure according to GC), prepared according to Example 1, 150 ml of xylene, 31 g (0.23 mol) of paraldehyde and 0.6 g of para-toluenesulfonic acid were charged to a 500 ml stirrer fitted with water separator, reflux condenser and thermometer, heated to boiling (160° C.) and stirred under reflux for a period of 4 h. A total of 7.2 ml of water was eliminated. After this time, the mixture was cooled to 20° C. and washed until neutral with sodium carbonate solution and water, and the solvent was distilled off under reduced pressure, leaving 72 g of crude product (87.8% pure according to GC).

GC conditions: see Example 2

(+/−) 4a $R_t$=28.81 min=33.12%

(+/−) 4b $R_t$=29.32 min=54.68%

(+/−) 4a : (+/−) 4b ratio=38:62

Thus, at the high reaction temperature chosen, significantly smaller amounts of the sensorially valuable cis compound were produced.

EXAMPLE 11

Alternative Preparation of (±)-2-methyl-4-phenyl-1,3-dioxolane (4) (reaction temperature: −20° C. to −15° C.)—FIG. 1

2.76 g (20 mmol) of (±)-1-phenyl-1,2-ethanediol (3) (90% pure according to GC), prepared according to Example 1, 10 ml of ether, and 20 mg of para-toluenesulfonic acid were charged to a 100 ml stirrer fitted with reflux condenser, thermometer and dropping funnel, and cooled to −20° C., and 1.32 g (30 mmol) of acetaldehyde were added dropwise over the course of 15 min, a temperature of −15° C. in the reaction mixture not being exceeded. The mixture was then stirred at −20° C. to −15° C. over a period of 6 h, washed until neutral with sodium carbonate solution and water and dried over sodium sulfate, and the solvent was distilled off under reduced pressure, leaving 2.91 g of crude product (89.2% pure according to GC).

GC conditions: see Example 2

(+/−) 4a $R_t$=28.80 min=71.4%

(+/−) 4b $R_t$=29.20 min=17.8%

(+/−) 4a:(+/−) 4b ratio=80:20

Thus, the formation of the sensorially valuable cis compound was greatly preferred at the low reaction temperature chosen.

EXAMPLE 12

Alternative Preparation of (±)-2-methyl-4-phenyl-1,3-dioxolane (4) (reaction temperature: −70° C.)—FIG. 1

2.76 g (20 mmol) of (±)-1-phenyl-1,2-ethanediol (3) (90% pure according to GC), prepared as in Example 1, 10 ml of ether and 20 mg of para-toluenesulfonic acid were charged to a 100 ml stirrer fitted with reflux condenser, thermometer and dropping funnel and cooled to −70° C., and, at this temperature, 1.32 g (30 mmol) of acetaldehyde were added dropwise over the course of 30 minutes. The mixture was then stirred at 70° C. for a period of 30 h, washed until neutral with sodium carbonate solution and water and dried over $Na_2SO_4$, and the solvent was distilled off under reduced pressure, leaving 2.83 g of crude product (78.3% pure according to GC).

GC conditions: see Example 2

(+/−) 4a $R_t$=28.78 min=70.5%

(+/−) 4b $R_t$=29.18 min=7.8%

(+/−) 4a:(+/−) 4b ratio=90:10

The formation of the sensorially valuable cis compound was thus extremely greatly preferred at the very low reaction temperature chosen.

EXAMPLE 13

Odor Description of Acetals 4, (+/−) 4a, (+/−) 4b, 7, 8, 11, 12

The odor evaluation was carried out using smelling strips by a panel of experts on the basis of 10% strength ethanolic solutions of the acetals.

Distillate—metal packed column 4 from Example 2
    Strong, floral, hyacinths, styrene, indole, green, narcotic, chocolate note
    After-odor: woody, ozone-like Distillate—Fischer Spaltrohr® column (+/−) 4a from Example 2
    Strong, indole, animal, styrene, styrax, hyacinths Distillate—Fischer Spaltrohr® column (+/−) 4b from Example 2
    Weak, animal, distinct chocolate note 7 from Example 7:
    Strong, clear, indole, rose-jasmine, the strongest- and best-smelling enantiomer 8 from Example 7:
    Floral, woody, diphenyl ether, rose, animal, chocolate note 11 from Example 8:
  Styrene, indole, skatole, hyacinths
12 from Example 8:
  Floral, lilac, woody, orange liquid, chocolate note

EXAMPLE 14

Odor Threshold Determination for Acetals 7, 8, 11, 12

The odor threshold determination was carried out by an expert panel of 20 test subjects. The odor threshold in water was determined.
7 from Example 7
  Mean: 125 µg/l
8 from Example 7
  Mean: 384 µg/l
11 from Example 8
  Mean: 384 µg/l
12 from Example 8
  Mean: 589 µg/l

The invention claimed is:

1. A fragrance composition comprising:
one part by weight of
  (2S,4R)-2-methyl-4-phenyl-1,3-dioxolane and/or
  (2R,4S)-2-methyl-4-phenyl-1,3-dioxolane
and less than one part by weight of
  (2R,4R)-2-methyl-4-phenyl-1,3-dioxolane and/or
  (2S,4S)-2-methyl-4-phenyl-1,3-dioxolane,
wherein the composition comprises at least 90% of the cis-isomer.

* * * * *